(12) United States Patent
Krilis (10) Patent No.: US 6,936,430 B1
(45) Date of Patent: Aug. 30, 2005

(54) PROCOAGULANT ASSAY (75) Inventor: Steven Krilis, Hunters Hill (AU)

(73) Assignee: South Eastern Sydney Area Health Service, Dolls Point (AU)

( * ) Notice: Subject to any disclaimer, the term of this patent is extended or adjusted under 35 U.S.C. 154(b) by 0 days.

(21) Appl. No.: 09/958,667

(22) PCT Filed: Apr. 12, 2000

(86) PCT No.: PCT/AU00/00309

§ 371 (c)(1),
(2), (4) Date: Nov. 28, 2001

(87) PCT Pub. No.: WO00/62077

PCT Pub. Date: Oct. 19, 2000

(30) Foreign Application Priority Data

Apr. 12, 1999 (AU) .............................................. PP 9712

(51) Int. Cl.[7] .................................................. C12Q 1/56
(52) U.S. Cl. ........................................ 435/13; 435/214
(58) Field of Search ............................. 435/13, 23, 214; 356/39; 422/73; 436/69; 530/381, 384; 600/369

(56) References Cited

U.S. PATENT DOCUMENTS

| 5,192,689 A | * | 3/1993 | Hemker et al. ................ 436/69 |
| 5,525,477 A | * | 6/1996 | Hassouna ..................... 435/13 |
| 5,618,713 A | * | 4/1997 | Zettlmeissl et al. ......... 435/226 |
| 5,705,198 A | | 1/1998 | Triplett et al. |
| 6,429,017 B1 | * | 8/2002 | Toh et al. ...................... 436/69 |
| 2003/0003515 A1 | * | 1/2003 | Farrell et al. ................ 435/7.9 |

FOREIGN PATENT DOCUMENTS

| EP | 0 420 332 A | | 4/1991 |
| JP | 2811799 | * | 10/1998 |
| SU | 1492287 | * | 7/1989 |
| WO | WO 91/01383 A | | 2/1991 |
| WO | WO 92/07954 | | 5/1992 |

OTHER PUBLICATIONS

Rijkers D. et al. Prevention of the Influence of Fibrin and Alpha2–Macroglobulin in the Continuous Measurement of the Thrombin Potential. Thrombosis Research 89(4)161–169, 1998.*

Hemker H. et al. Continuous Registration of Thrombin Generation in Plasma, Its Use for the Determination of the Thrombin Potential. Thrombosis and Haemostasis 70(4)617–624, 1993.*

Wielders S. et al. the Routine Determination of the Endogenous Thrombin Poteintal, First Results in Different Forms of Hyper and Hypocoagulability. 77(4)629–636, 1997.*

Hemker H. et al. Thrombin Generation in Plasma: Its Assessment via the Endogenous Thrombin Potential. Thrombosis and Haemostasis 74(1)134–138, 1995.*

Rijkers, D.T.S., et al; "Prevention of the Influence of Fibrin and $\alpha_2$–Macroglobulin in the . . . Endpoint Determination of the Optical Density"; Thrombosis Research, vol. 89, No. 4, 1998, pp. 161–169, XP002917872; ISSN: 0049–3848.

Howie, P.W. et al; "A Method of Antithrombin Estimation using Plasma Defibrinated with Ancrod"; British Journal of Haematology; vol. 25, 1973, pp. 101–110, SP002221488.

Patent Abstracts of Japan; vol. 1995, No. 03; Apr. 28, 1995; & JP 06 331628 A (Sekisui Chem. Co. Ltd. ), Dec. 2, 1994; abstract.

Hemker, H.C. et al; "Continuous Registration of Thrombin Generation in Plasma, Its Use for the Determination of the Thrombin Potential"; Thrombosis and Haemostasis, Stuttgart, DE, vol. 70, No. 4, 1993, pp. 617–624, XP000567560; ISSN: 0340–6245.

Hunt, J.E., et al; "A Phospholipid–$\beta_2$–Glycoprotein I Complex is an Antigen for Anticardiolipin Antibodies Occuring in Autoimmune Disease But Not with Infection"; *Lupus* 1(2); pp. 75–81 (1992).

Wielders, S., et al; "The Routine Determination of the Endogenous Thrombin Potential, First Results in Different Forms of Hyper–and Hypocoagulability"; *Thromb. Haemost.*; 77(4); pp. 629–636 (1997).

Forastiero, R.R., et al; "Relationship of Anti $\beta_2$–glycoprotein I and Anti Prothrombin Antibodies to Thrombosis and Pregnancy Loss in Patients with Antiphospholipid Antibodies"; *Thromb. Haemost*; 78(3); pp. 1008–1014 (1997).

Schultz, D.R.; "Antiphospholipid Antibodies: Basic Immunology and Assays"; *Seminars in Arthritis and Rheumatism*; 26(5); pp. 724–739 (1997).

Hemker, H.C., et al; "Thrombin Generation in Plasma: Its Assessment Via the Endogenous Thrombin Potential"; *Thromb Haemost.*; 74(1); pp. 134–138 (1995).

Derwent Abstract Accession No. 95–054707/08, Class S03; JP 0–6331628 (Sekisui); Dec. 2, 1994.

* cited by examiner

*Primary Examiner*—Ralph Gitomer
(74) *Attorney, Agent, or Firm*—Nixon & Vanderhye (57) ABSTRACT

Method of detecting coagulation abnormalities in a plasma sample by (a) determining a test rate of thrombin generation over a given time interval by reacting an activator of thrombin with defibrinated normal plasma in the presence of a defibrinated test plasma sample; (b) determining a control rate of thrombin generation over substantially the same time interval in step (a) by reacting the same activator of thrombin with defibrinated normal plasma in the absence of any defibrinated test plasma; and (c) comparing the rates of thrombin generation between test step (a) and control step (b) such that any significant difference between the two thrombin generation rates being indicative of a coagulation abnormality in the test plasma.

15 Claims, 9 Drawing Sheets

PROCOAGULANT ASSAY

This application is a National Stage application filed under Rule 371 based on PCT/AU00/00309 filed Apr. 12, 2000, which claims priority to Australia application PP 9712 filed Apr. 12, 1999.

TECHNICAL FIELD

The present invention relates generally to blood coagulation assays and in particular to a method of detecting blood coagulation/clotting abnormalities in individuals.

BACKGROUND ART

Antiphospholipid antibodies (aPA) are a heterogeneous group of circulating autoantibodies that were originally thought to bind negatively-charged phospholipids. These autoantibodies have been associated with a range of clinical associations, in particular thrombotic events. Despite extensive literature in the pathogenic mechanisms, which explain the association between aPA and the major clinical manifestations of the antiphospholipid syndrome, mainly thrombosis, are unknown. These autoantibodies were originally thought to bind negatively-charged phospholipids and could be demonstrated in a variety of other clinical syndromes. However, in 1990 the present inventor demonstrated for the first time that these autoantibodies in fact bind β2-glycoprotein I (β2-GPI), a phospholipid binding plasma protein whose physiological role is unknown.

Currently there are two assay systems in clinical practice to identify these autoantibodies. The first assay uses the negatively-charged phospholipid most commonly cardiolipin to coat microtitre wells and antibodies detected in this assay are known as anticardiolipin (ACL) antibodies. This assay system detects anticardiolipin antibodies in autoimmune patients and also in a variety of infections which are not associated with thrombotic events. It appears now that the autoimmune ACL antibodies detected in the ELISA system are directed against β2-GPI, which is captured on the negatively charged surface. The anticardiolipin antibodies occurring in infections like malaria, syphilis, leprosy, tuberculosis are not associated with clinical thrombotic events are now known not to bind β2-GPI but in fact are directed against negatively-charged phospholipids and are thus true phospholipid antibodies. These antibodies are usually of low affinity and are dependent on charge as high salt concentrations eliminate their binding to cardiolipin.

The second type of assay used is one that looks at the prolongation of in-vitro clotting assays. Autoantibodies that prolong phospholipid-dependent clotting tests which are not corrected by adding normal plasma and are neutralised by the addition of phospholipid are defined as lupus anticoagulants (LA). Patients may have either of these antibody subtypes or both activities. More recently the use of β2-GPI in an ELISA identifies the autoimmune ACL antibodies since the infective ACL antibodies do not bind in this assay system. However, for clinical testing, both assays have to be utilised as patients with the antiphospholipid syndrome may be missed if only one assay system is used.

The present inventor has now developed an in-vitro assay system which is simple, will identify both ACL and LA type antibodies, would discriminate between infective and autoimmune type ACL autoantibodies and may be used to identify patients at risk of clinical thrombotic events.

DISCLOSURE OF INVENTION

The present invention consists in a method of detecting coagulation abnormalities in a plasma sample, the method comprising:

(a) determining a test rate of thrombin generation over a given time interval by reacting an activator of thrombin with defibrinated normal plasma in the presence of a heat defibrinated test plasma sample;
(b) determining a control rate of thrombin generation over substantially the same time interval in step (a) by reacting the same activator of thrombin with defibrinated normal plasma in the absence of any defibrinated test plasma; and
(c) comparing the rates of thrombin generation between test step (a) and control step (b) such that any significant difference between the two thrombin generation rates being indicative of a coagulation abnormality in the test plasma.

In preferred forms of the present invention, the activator of thrombin is selected from thromboplastin, kaolin, Russell Viper venom, silica, or other similar reagents. Preferably, the activator is thromboplastin. It will be appreciated, however, that other activators that cause the generation of thrombin from defibrinated plasma would also be suitable for the present invention.

The term "normal plasma" is used to define the use of a standard supply of defibrinated plasma as the source for thrombin generation in steps (a) and (b). Normal plasma may be any defibrinated plasma as long that it is a suitable source for thrombin generation by the thrombin activator used in the test.

The present inventor has found that the presence of antibodies to β2-GPI in a plasma sample, which are known to inhibit or lower blood coagulation in vivo, will adversely effect the rate of thrombin production or generation from defibrinated plasma in a procoagulant in vitro assay. Therefore, defibrinated plasma from patients with antibodies to β2-GPI, when tested by the present invention, will lower the rate of thrombin production compared to the control test (step (b)). It will also be appreciated that enhanced clotting ability in plasma samples will also be detected by the present invention by causing an increase in the rate of thrombin generation as compared to the control test.

In a preferred embodiment of the present invention, the time interval is about 20 minutes. It will be appreciated, however, that the time interval is discretionary but should be long enough to allow at least some generation of thrombin from the plasma to be induced by the thrombin activator used in the assay.

Preferably the thrombin generation is measured by adding a substrate which is converted by the generated thrombin to a detectable product. One suitable substrate which can be detected photometrically is spectrozyme. It will be appreciated, however, that other substrates would also be suitable.

The reaction to generate thrombin from the defibrinated plasma may further require cofactors, buffers, salts and the like and therefore, the present invention would include within its scope the use of such compounds and chemicals to assist in the production of thrombin from the defibrinated normal plasma.

A chromogenic assay originally described by Lando et al, (1986) journal of Immunological Methods 89: 131–139 has been found to be particularly suitable to determine the rate of thrombin generation in the assay. In essence, this is a measure of in vitro thrombin generation over a twenty minute period detected by a chromogenic substrate. When thrombin formation measured in optical density units on the Y axis is plotted over time measured in minutes on the X axis, a sigmoidal curve is derived. A shift in the curve to the left indicates accelerated thrombin generation and a shift to the right indicates inhibition of thrombin formation. Such changes can be quantified by expressing the results as a ratio of the ratio of the normal curve using the mean of three data points on the linear portion of the curve.

The basis of the assay is that thrombin is generated by thromboplastin in the presence of defibrinated normal plasma. Thrombin then converts a colourless substrate to yellow whose generation can be followed as a time course on an ELISA plate reader.

When using a chromogenic assay, preferably thrombin formation in steps (a) and (b) is measured in optical density units, the units obtained placed on a Y axis and plotted over time measured in minutes on an X axis such that a sigmoidal curve is derived.

In one preferred form, the method according to the present invention detects a coagulation abnormality which indicates a decreased clotting potential. The decreased clotting potential can arise from clinical situations where there is consumption of coagulation factors. Examples of such clinical situations include sepsis, severe trauma and autoimmune conditions.

In another preferred form, the method according to the present invention detects a coagulation abnormality which indicates an increased clotting potential. The increased clotting potential can arise from autoantibodies to β2-GPI, prothrombin or other antigens that induce antiphospholipid antibodies to occur, lupus or other autoimmune conditions, or in isolation.

Accordingly, in a more preferred form, the present invention consists in a method of detecting coagulation abnormalities in a plasma sample, the method comprising:
(a) determining a test rate of thrombin generation over a given time interval by reacting thromboplastin with defibrinated normal plasma in the presence of a heat defibrinated test plasma sample;
(b) determining a control rate of thrombin generation over substantially the same time interval in step (a) by reacting thromboplastin with defibrinated normal plasma in the absence of any defibrinated test plasma; and
(c) comparing the rates of thrombin generation between test step (a) and control step (b) such that any significant difference between the two thrombin generation rates being indicative of a coagulation abnormality in the test plasma.

The present invention allows the detection of both ACL and LA type antibodies in the one test by utilising thrombin generation from normal defibrinated serum. The present invention arises in part form the surprising finding that testing or screening for clotting abnormalities can be achieved by using defibrinated plasma. The present invention has the potential to greatly simplify clinical testing for clotting abnormalities in patients and in individuals that may not have clinical symptoms. The present invention results in only one test being required to determine whether a serum sample has ACL and/or LA type antibodies.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described in the following examples with reference to the accompanying drawings.

MODE FOR CARRYING OUT THE INVENTION

In Vitro Procoagulant Assay (PCGA)

A chromogenic assay originally described by Lando et al. (1986) Journal of Immunological Methods 89: 131–139 was used to determine the rate of thrombin generation over time. In essence, this is a measure of in vitro thrombin generation over a twenty minute period detected by a chromogenic substrate. When thrombin formation measured in optical density units on the Y axis is plotted over time measured in minutes on the X axis, a sigmoidal curve is derived. A shift in the curve to the left indicates accelerated thrombin generation and a shift to the right indicates inhibition of thrombin formation. Such changes can be quantified by expressing the results as a ratio of the ratio of the normal curve using the mean of three data points on the linear portion of the curve.

The present inventor has used this assay system to look at a number of antibody populations:

1: Mouse monoclonal anti-human β2-GPI derived by immunising with native β2-GPI.
2. Naturally occurring anti-β2-GPI antibodies from an animal model of the antiphospholipid syndrome.
3. Monoclonal antibody derived from a patient with the antiphospholipid by Ebstein-Barr virus (EBV) transformation of peripheral blood Lymphocytes.
4. Plasma from antiphospholipid syndrome patients.
5. Purified antibodies from antiphospholipid syndrome patients.
6. Normal control plasma.
7. Normal control immunoglobulin.
8. Polyclonal antibody to prothrombin.

All the monoclonal antibodies tested that had reactivity to human β2-GPI inhibited thrombin generation to varying degrees. The monoclonal antibodies from the animal model of the antiphospholipid syndrome NZW BXBS BF1 also caused inhibition of binding but at higher concentrations of antibody. All five human monoclonal antibodies derived from peripheral blood lymphocytes inhibited thrombin generation. All the human plasma and purified antibodies behave like the monoclonal anti-β2-GPI antibodies in that they inhibited thrombin generation. In addition, there was a significant association between the level of anti-62-GPI antibodies and inhibition of in-vitro thrombin generation.

Figure 1:
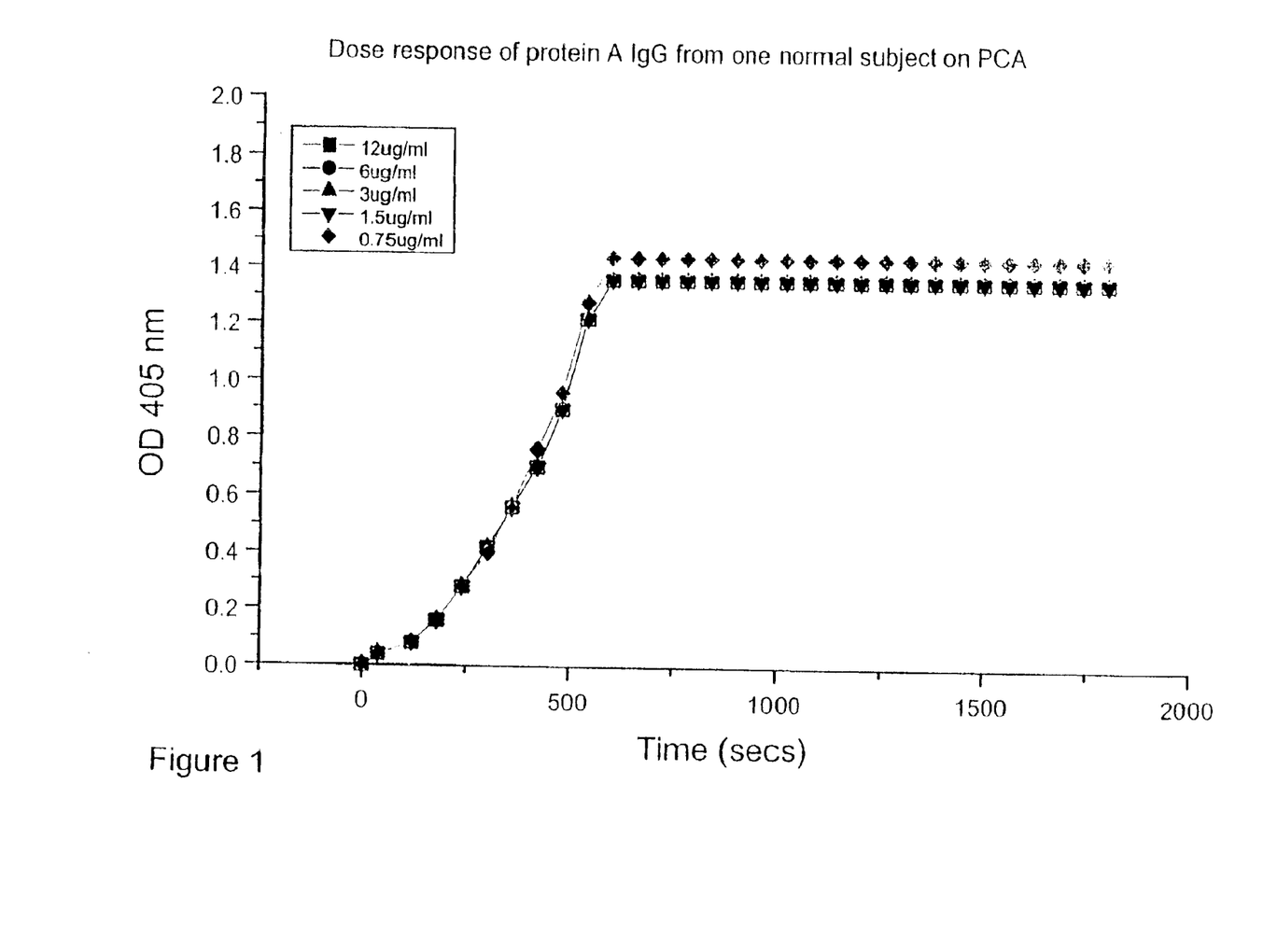
FIG. 1 shows a dose response of IgG from a normal individual purified by protein A at dose response from 0.75 µg/ml to 12 µg/ml which showed that there was no effect on the procoagulant assay (PCA) compared to thromboplastin alone without antibody.
Figure 2:
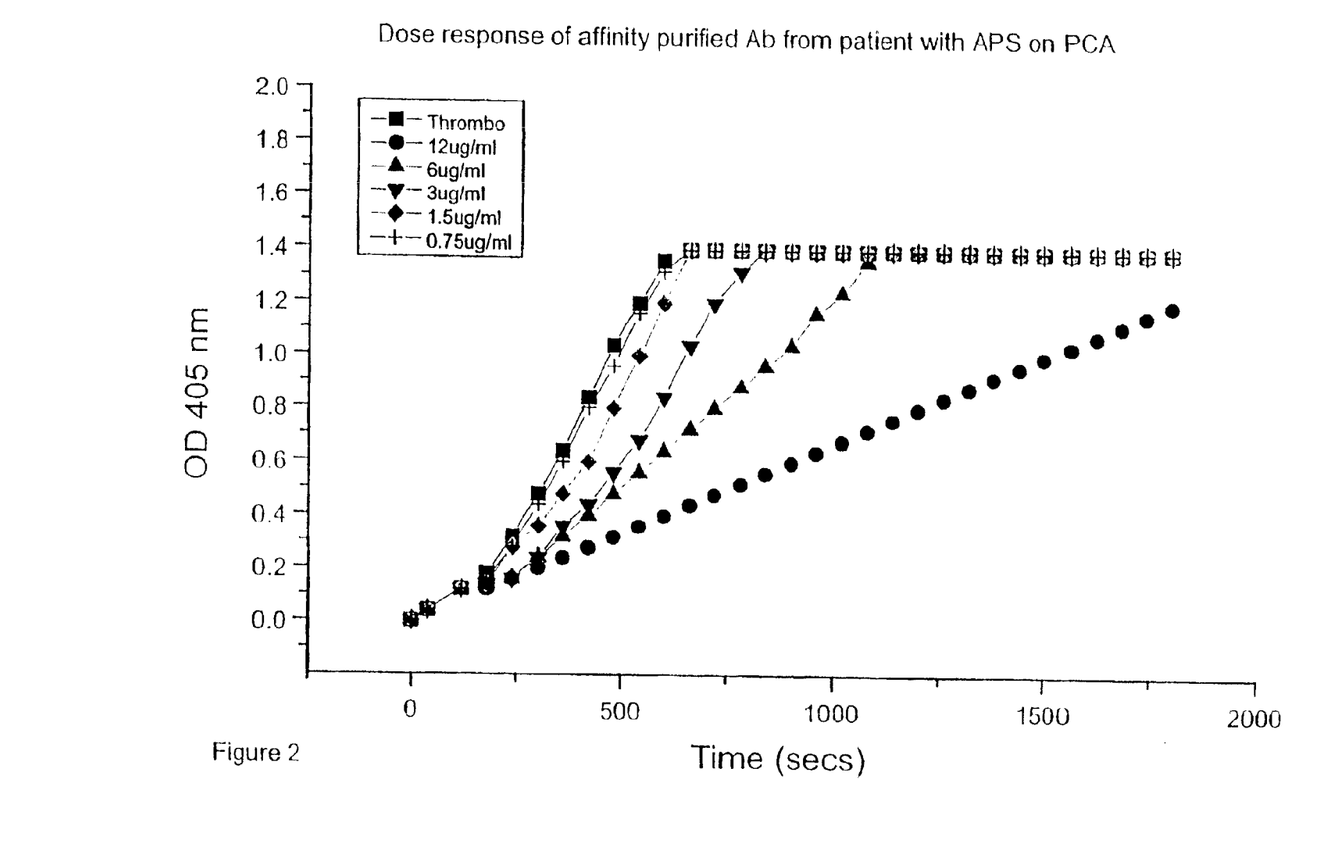
FIG. 2 shows a dose response of affinity purified antibody from a patient with the antiphospholipid syndrome with clinical disease on PCA. The results show a dramatic effect on dose response from, 0.75 µg/ml to 12 µg/ml compared to thromboplastin (THP) alone. The shift to the right implying inhibition of thrombin generation with the greatest effect seen at 12 µg/ml.
Figure 3:
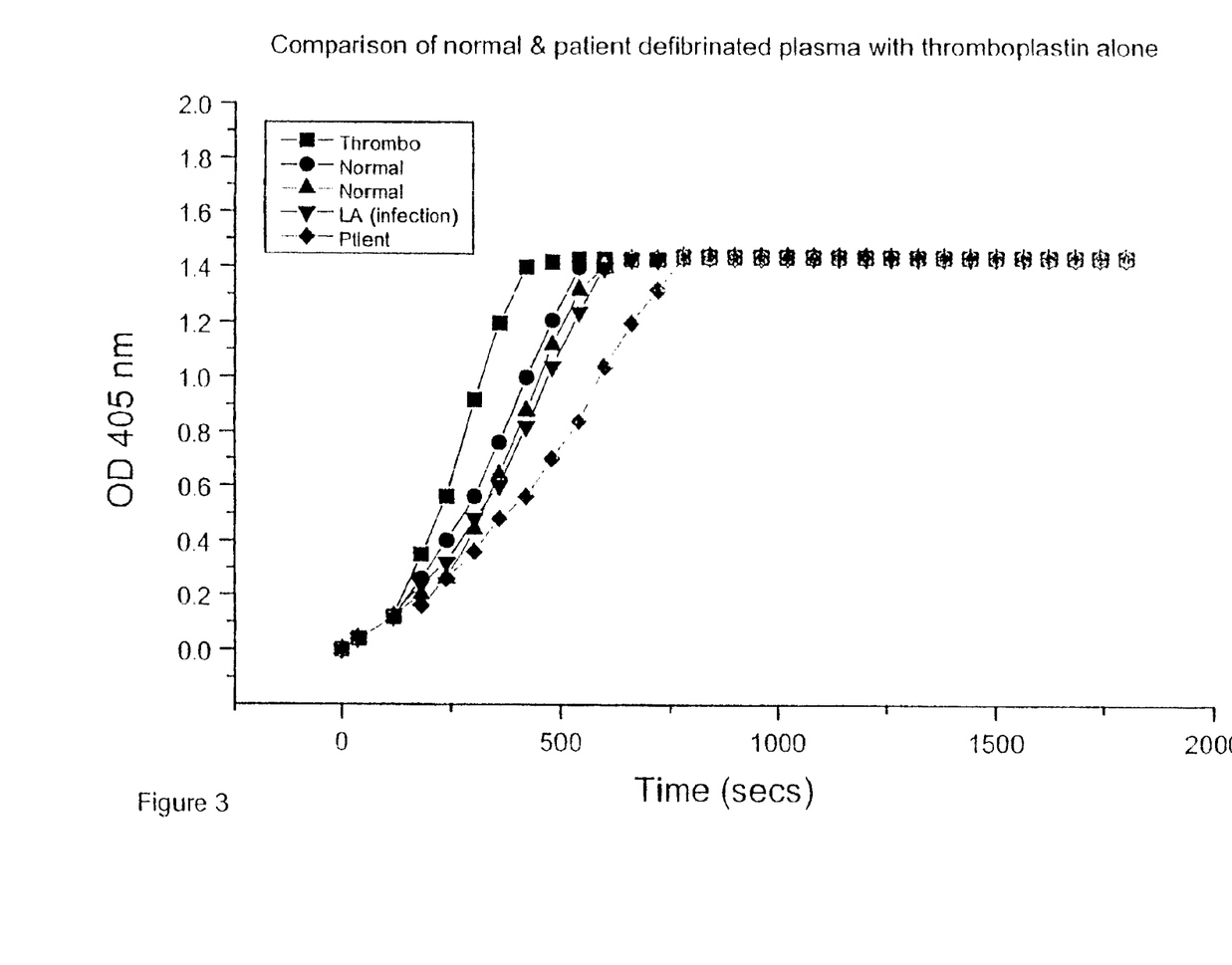
FIG. 3 shows results from a patient with clinical syndromes compared to a standard curve of TPH alone and two normals, with a preparation obtained from a patient with infectious disease (typhoid) where you can get positivity in the lupus anticoagulant assay showing that there is minimal effect on the curve.
Figure 4:
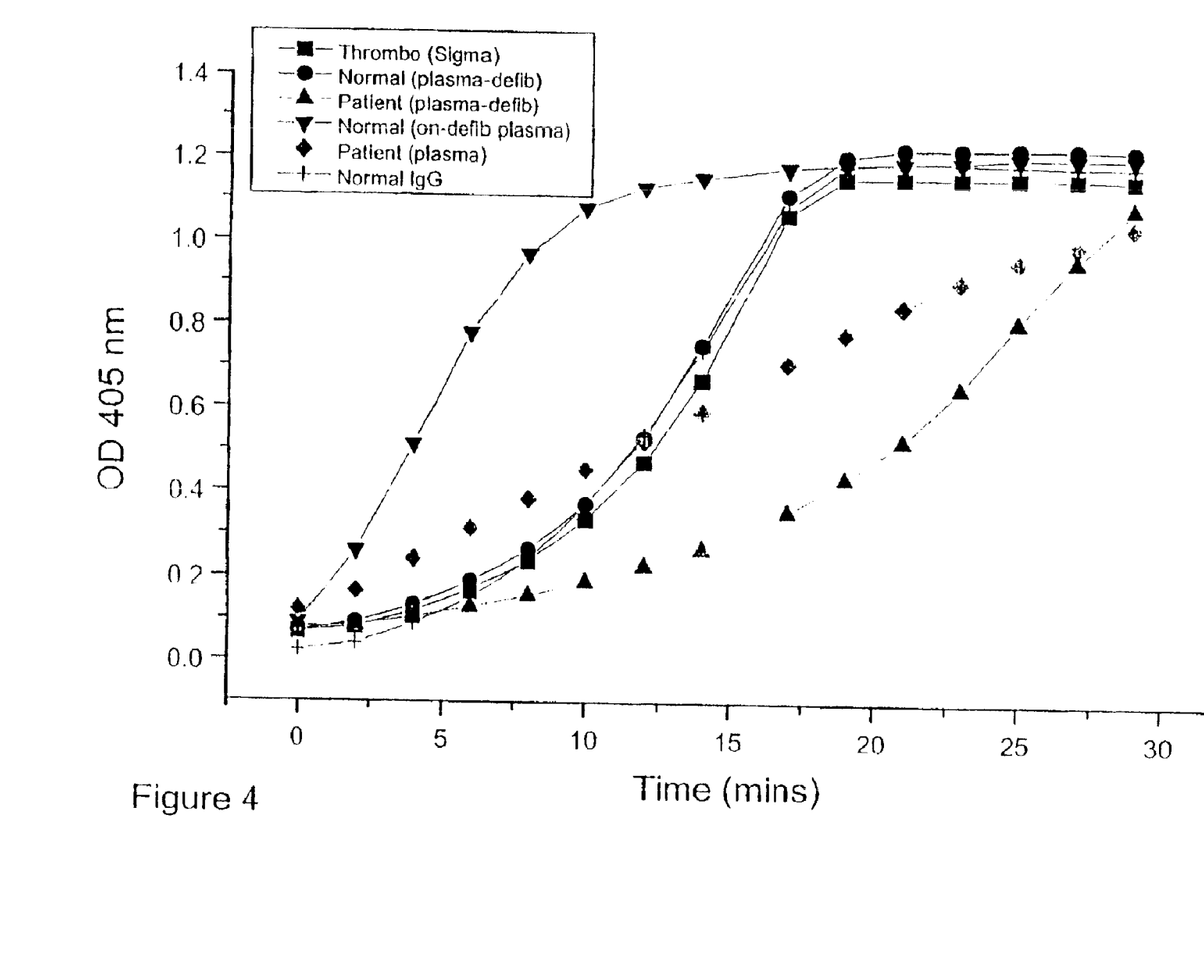
FIG. 4 shows the effect of using undefibrinated plasma in the assay. Normal plasma not defibrinated shifts the curve to the left. Normal plasma defibrinated is the same as thromboplastin standard curve as is purified normal IgG. Patient plasma non-defibrinated shifts the curve to the right but not as dramatically as patient plasma defibrinated implying that defibrination of plasma is important in this assay system.
Figure 5:
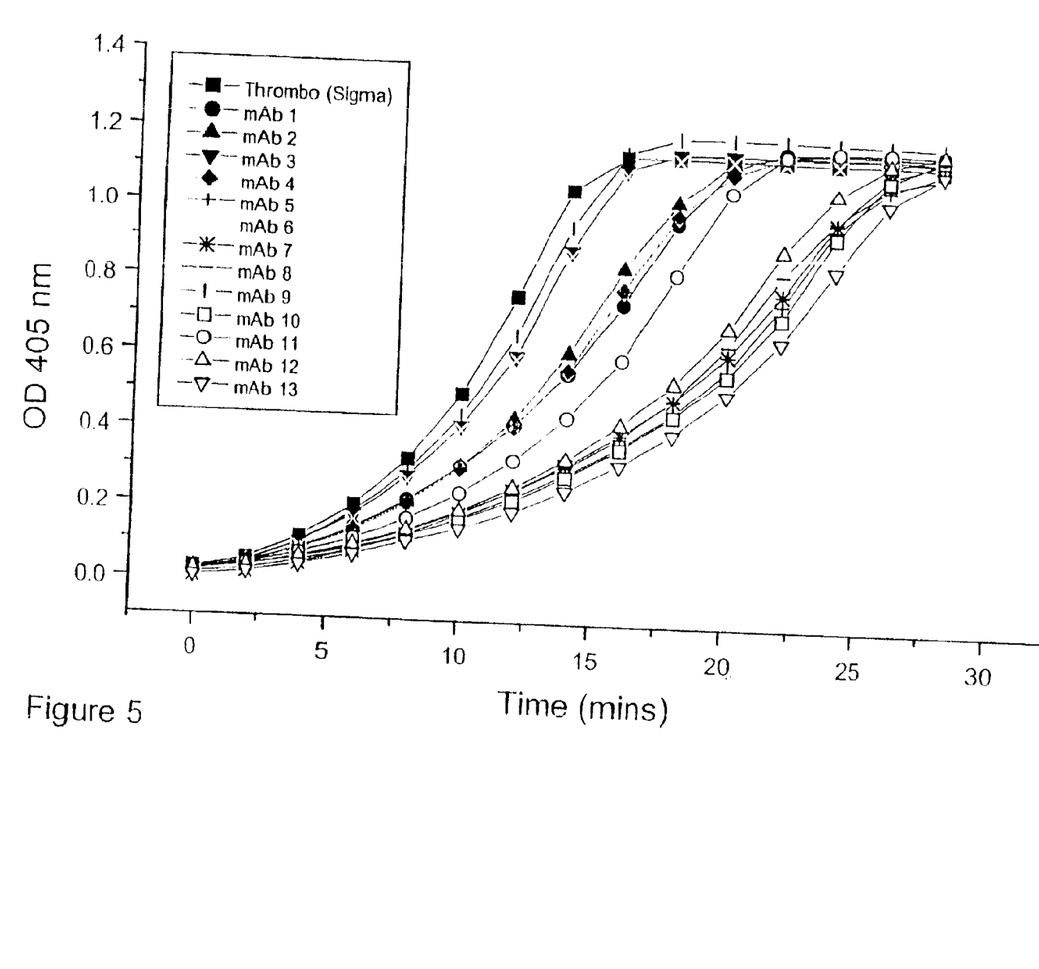
FIG. 5 shows a range of monoclonal antibodies to β2-glycoprotein 1 that have been derived via injecting mice with human β2-GPI. In every case, the antibodies shift the curve to the right at varying degrees. Some, like the inverted triangles, dramatically cause a shift to the right implying potent inhibition of thrombin generation. Interestingly every one of the monoclonal antibodies tested caused a shift to the right.
Figure 6:
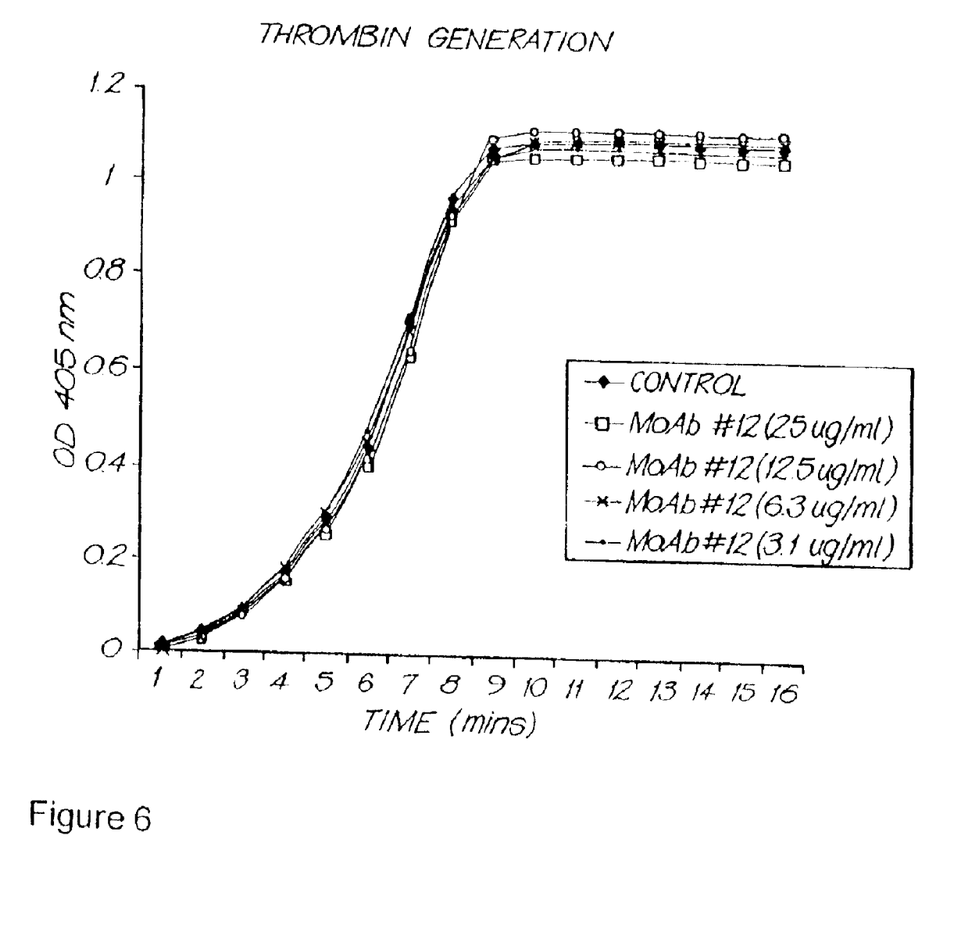
FIG. 6 shows a control monoclonal antibody not derived against β2-GPI of the same isotype as the monoclonal antibodies in FIG. 4 which does not shift the curve at all even with increasing doses up to 25 µg/ml.
Figure 7:
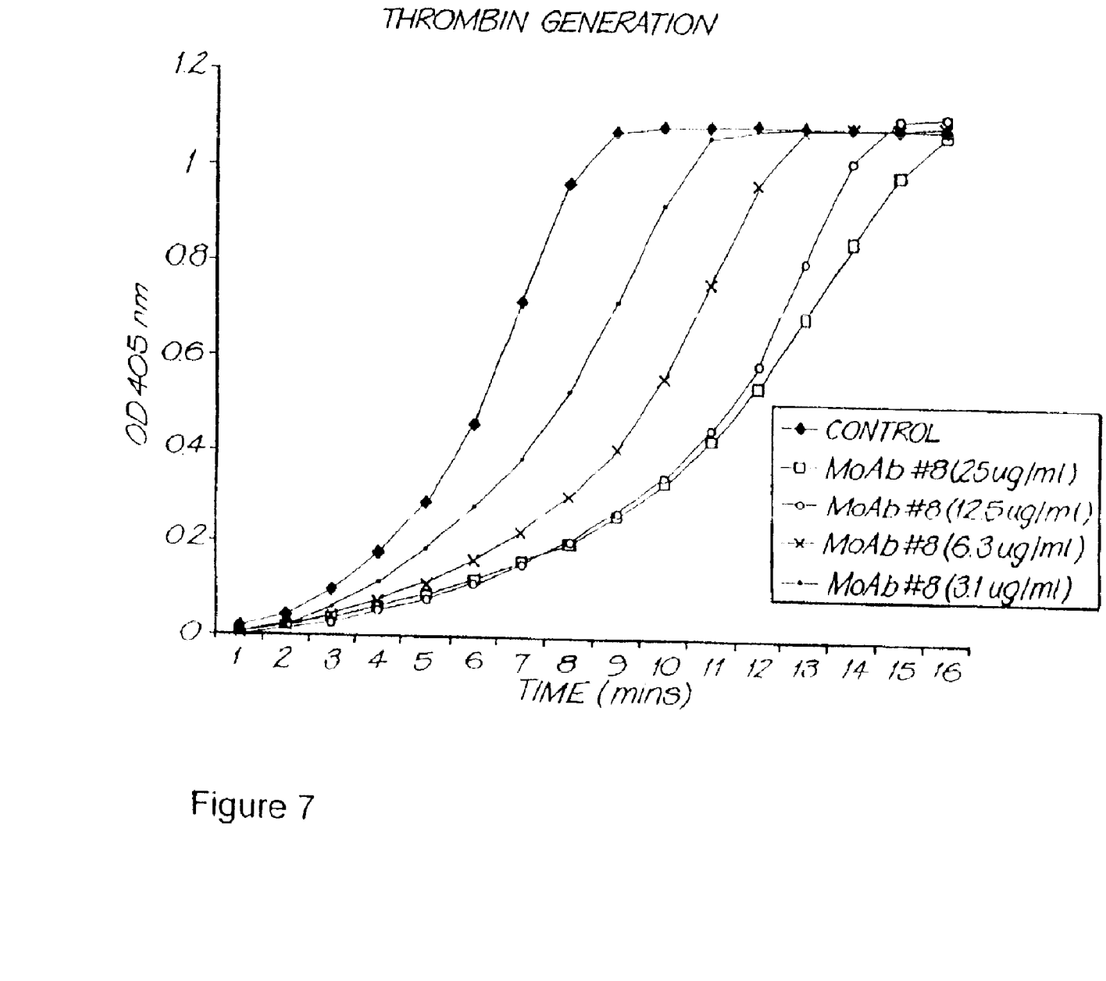
FIG. 7 shows a monoclonal antibody to β2-glycoprotein 1 dose response showing a marked dose response effect from 3.1 µg/ml to 25 µg/ml.
Figure 8:
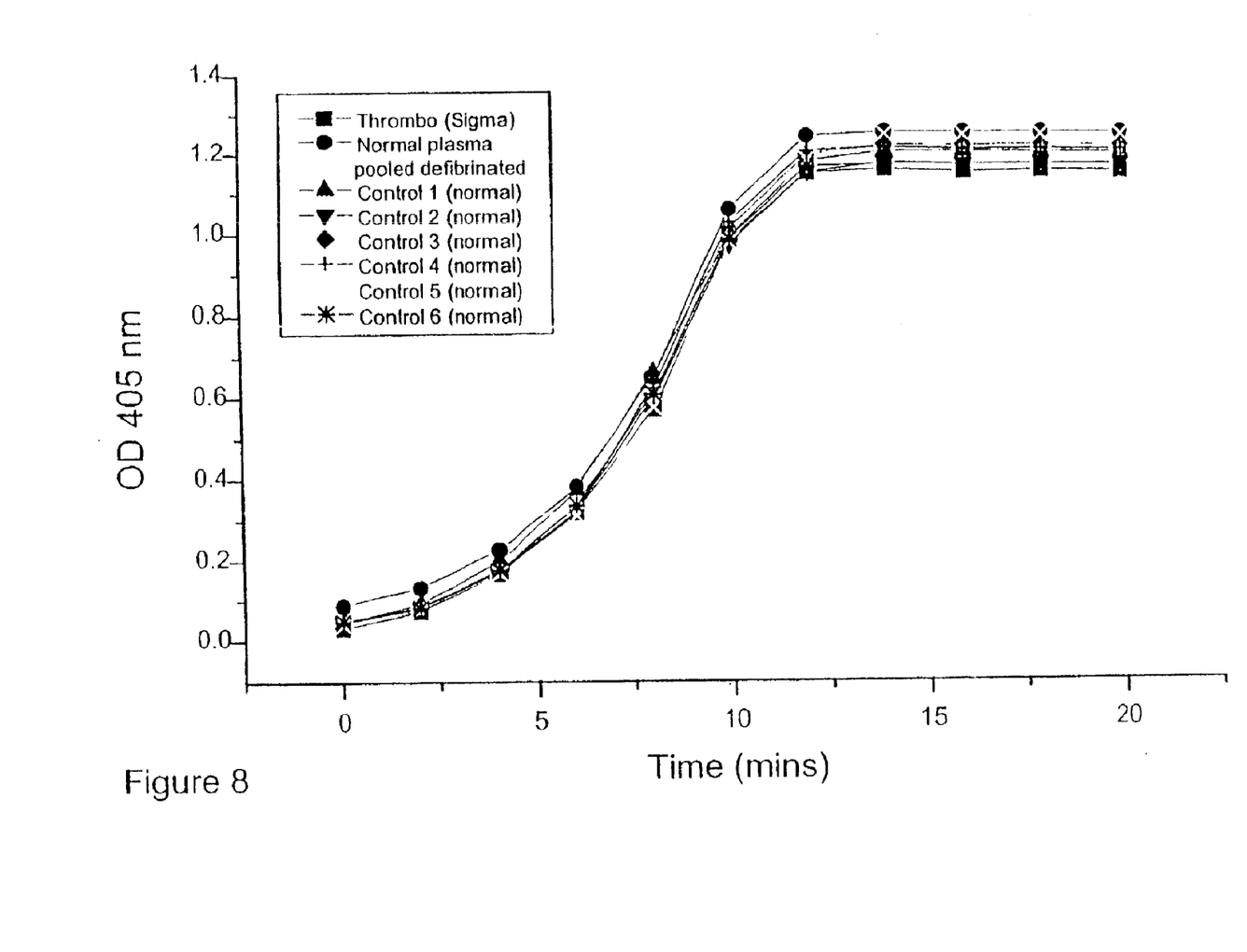
FIGS. 8 and 9 show the effect of six normal defibrinated plasmas and a pooled normal plasma from ten different individuals also defibrinated on the effect of thrombin generation. The results show that there is no difference between those normals and the normal standard curve. Whereas in FIG. 9, there are a range of effects seen using the different patient populations and comparing this to thromboplastin alone and the normal plasma pool the great majority cause a shift to the right. An antibody to prothrombin which has LA activity also has been demonstrated to shift the thrombin generation curve to the right.
Figure 9:
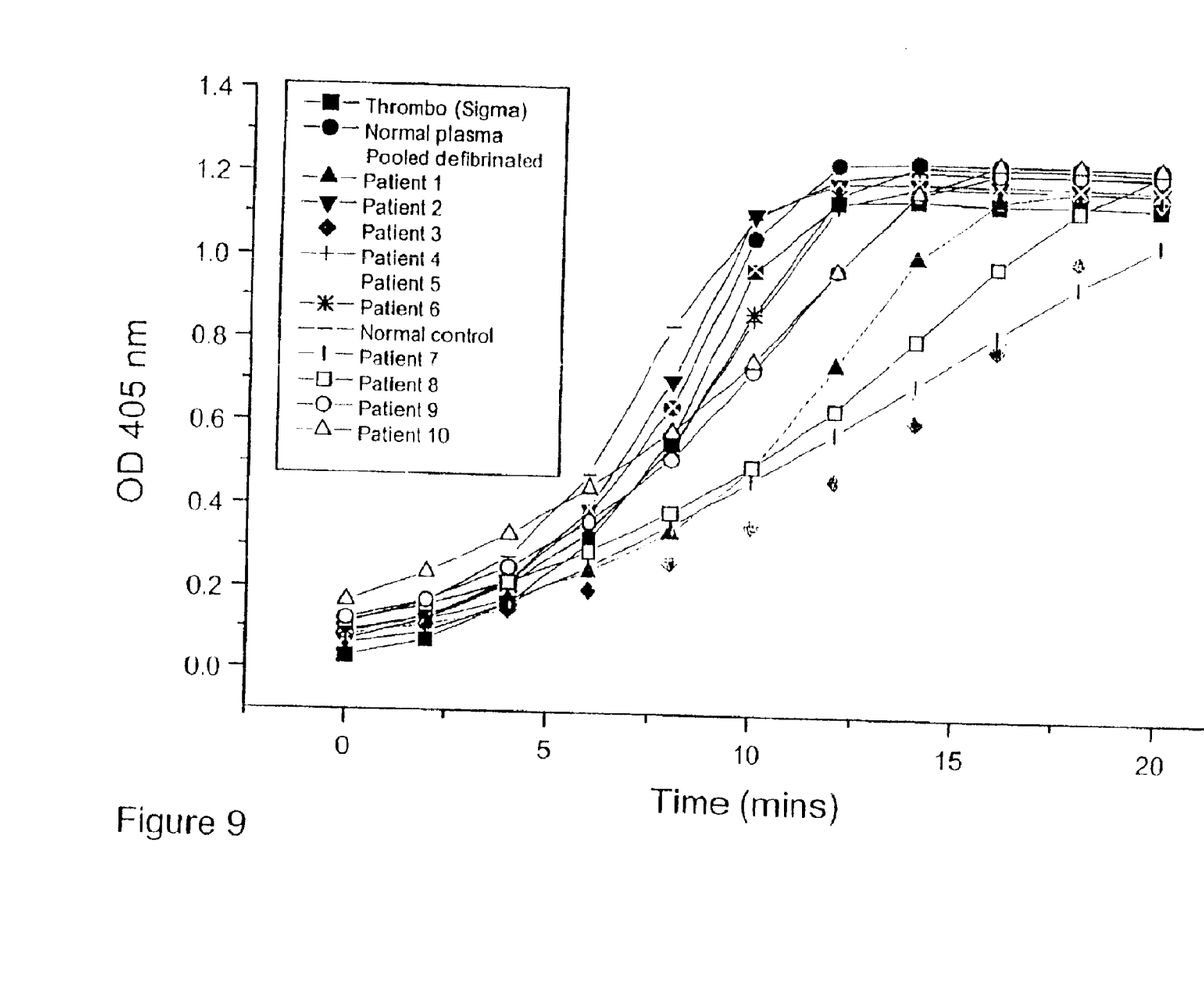

The results of the experiments are shown in FIGS. 1 to 9 and explained by the Figure legends.

The basis of the assay is that thrombin is generated from thromboplastin in the presence of defibrinated plasma. Thrombin then converts a colourless substrate to yellow whose generation can be followed as a time course on an ELISA plate reader.

Defibrinated Plasma Preparation

Collect blood in 4.5 ml Na citrate vacutainer tubes. Typically 5–10 tubes from 3–5 normal laboratory workers were used. Tubes spun at 3000×g for 20–30 min. Plasma is pooled and filtered through 0.2 μm syringe filter. Aliquots are placed into 50 ml falcon tubes and placed into a shaking water bath at 53° C. for 20 minutes. The plasma should become cloudy. This step is important as the PCA will not work effectively if the plasma has not been sufficiently defibrinated. Temperature is, important as defibrination will not occur at 50° C. Plasma is spun @ 3000×g for 10 min. Supernatant is collected and aliquoted 2 ml/tube and frozen @ −20° C. Thawed defibrinated plasma can be used if its been stored O/N at 4° C. but oenerallv not for longer periods as the activity tends to decrease.

Thromboplastin (THP)

Purchased from Sigma #T7280: 'thromboplastin with calcium'. To a bottle of lyophilised powder is added 4 ml of deionised water. Stored at 4° C. or up to a month. Do not freeze.

Spectrozyme (American Diagnostica #238L) (H-D-hexahydrotyrosol-alanyl-arginine-para-nitroanilide diacetate) 50 uMole/bottle. Add 10 ml water to powder to obtain 5 mM. Store stock @ −20° C. and aliquots in use at 4° C. for up to 1 week.

Calcium chloride 1M stock in water.
0.9% NaCl
Linbro titertek ELISA 96 well plates
Procedure 1: 25 μl thromboplastin (TBP) per well (diluted 1/10 in 0.9% NaCl).
2: 25 μl of test antibody diluted in 0.9% NaCl (typically added at 50 μg/ml, final concentration 6.25 μl/ml).
3: 50 μl of pooled defibrinated plasma. (Some preparations need to be diluted as curves generated are too steep: current stock of defibrinated plasma at ¼ dilution in 0.9% NaCl)
4: Incubate at 37° C. for 10 min
5: 50 μl of spectrozyme diluted ⅕ in 0.9% NaCl at RT
6: 50 μl of 30 mM CaCl diluted in 0.9% NaCl at RT. Time starts on the addition of CaCl.

Absorbance read @ 405 nm every 2 minutes. A typical curve is a skewed S shape and the readings are stopped when a plateau is reached at ~OD of 1.2. A thromboplastin alone curve will flatten out after 20 minutes.

| Blank | Thromboplastin | Test |
|---|---|---|
| NaCl | THP | THP |
| NaCl | NaCl | teat sample |
| plasma | plasma | plasma |
| substrate | substrate | substrate |
| CaCl | CaCl | CaCl |

An advanced plate reader (eg Molecular Devices Spectro Max 250) is advantageous as it avoids tedious number crunching when transferring data from paper to a graphics program. In addition, it is possible to maintain temperature at 37° C. and have the plate shaken between readings. This would probably result in curves reaching a maximum sooner that may then require adjusting THP and/or defibrinated plasma concentrations to achieve a less steep curve.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of detecting coagulation abnormalities in a test plasma sample, the method comprising:
   (a) determining a test rate of thrombin generation over a given time interval by reacting an activator of thrombin with defibrinated normal plasma in the presence of a heat defibrinated test plasma sample;
   (b) determining a control rate of thrombin generation over substantially the same time interval in step (a) by reacting the same activator of thrombin with defibrinated normal plasma in the absence of any heat defibrinated test plasma; and
   (c) comparing the rates of thrombin generation between test step (a) and control step (b) such that any significant difference between the two thrombin generation rates being indicative of a coagulation abnormality in the test plasma sample.

2. The method according to claim 1 wherein the activator of thrombin is selected from the group consisting of thromboplastin, kaolin, Russell Viper venom, and silica.

3. The method according to claim 2 wherein activator is thromboplastin.

4. The method according to claim 1 wherein the time interval is 20 minutes.

5. The method according claim 1 wherein the thrombin generation is measured by adding a substrate which is converted by the generated thrombin to a detectable product.

6. The method according to claim 5 wherein the substrate is a chromographic substrate.

7. The method according to claim 6 wherein the substrate is H-D-hexahydrotyrosol-alanyl-arginine-para-nitroanilide diacetate.

8. The method according to claim 5 wherein thrombin formation in steps (a) and (b) is measured in optical density units, the units obtained placed on a Y axis and plotted over time measured in minutes on an X axis such that a sigmoidal curve is derived.

9. The method according to claim 8 wherein the shift in the curve to the left indicates accelerated thrombin generation and a shift to the right indicates inhibition of thrombin formation in the test plasma sample.

10. The method according to claim 9 wherein changes are quantified by expressing the results as a ratio of the ratio of the normal curve using the mean of three data points on a linear portion of the curve.

11. The method according to claim 1 wherein the coagulation abnormality is a decreased clotting potential.

12. The method according to claim 11 wherein the decreased clotting potential arises from clinical situations including sepsis, severe trauma, and autoimmune conditions.

13. The method according to claim 1 wherein the coagulation abnormality is increased clotting potential.

14. The method according to claim 13 wherein the increased clotting potential arises from autoantibodies to β2-GPI, prothrombin or other antigens that induce antiphospholipid antibodies to occur, lupus or other autoimmune conditions, or in isolation.

15. A method of detecting coagulation abnormalities in a test plasma sample, the method comprising:

a) determining a test rate of thrombin generation over a given time interval by reacting thromboplastin with defibrinated normal plasma in the presence of a heat defibrinated test plasma sample;

b) determining a control rate of thrombin generation over substantially the same time interval in step (a) by reacting thromboplastin with defibrinated normal plasma in the absence of any heat defibrinated test plasma; and c) comparing the rates of thrombin generation between test step (a) and control step (b) such that any significant difference between the two thrombin generation rates being indicative of a coagulation abnormality in the test plasma sample.

* * * * *